(12) United States Patent  
Marietti

(10) Patent No.: US 8,729,516 B2
(45) Date of Patent: May 20, 2014

(54) METHOD AND DEVICE FOR DETECTING METALS IN A FLUID

(75) Inventor: Yannick Marietti, Saint Antonin sur Bayon (FR)

(73) Assignee: STMicroelectronics (Rousset) SAS, Rousset (FR)

(*) Notice: Subject to any disclaimer, the term of this patent is extended or adjusted under 35 U.S.C. 154(b) by 344 days.

(21) Appl. No.: 13/252,055

(22) Filed: Oct. 3, 2011

(65) Prior Publication Data

US 2012/0080620 A1   Apr. 5, 2012

(30) Foreign Application Priority Data

Oct. 4, 2010  (FR) ...................... 10 03909

(51) Int. Cl.
*G01N 15/06* (2006.01)
*G01N 21/49* (2006.01)
*G01N 21/85* (2006.01)

(52) U.S. Cl.
USPC ...................... 250/573; 250/214.1; 250/208.2

(58) Field of Classification Search
USPC ................ 250/573, 574, 208.2, 214.1, 214 R
See application file for complete search history.

(56) References Cited

U.S. PATENT DOCUMENTS

| | | | |
|---|---|---|---|
| 5,133,901 A | | 7/1992 | Peterson et al. |
| 5,227,265 A | * | 7/1993 | DeBoer et al. ................. 430/41 |
| 2008/0204115 A1 | * | 8/2008 | Sugawara ...................... 327/512 |
| 2010/0039707 A1 | * | 2/2010 | Akahane et al. .............. 359/576 |

FOREIGN PATENT DOCUMENTS

WO   2009/123645 A1   10/2009

OTHER PUBLICATIONS

Aharoni, H., "Analysis of n+p silicon junctions with varying substrate doping concentrations made under ultraclean processing technology," J. Appl. Phys. 81(3):1270-1288, Feb. 1, 1997.

* cited by examiner

*Primary Examiner* — Francis M Legasse, Jr.
(74) *Attorney, Agent, or Firm* — Seed IP Law Group PLLC

(57) ABSTRACT

A method detects metallic atoms in a fluid. The method includes: placing, in a zone sheltered from light, a photodiode comprising a photosensitive surface in contact with a fluid to analyze; heating the photosensitive surface of the photodiode to a temperature sufficient to allow metallic atoms deposited on the photosensitive surface to migrate through this surface; acquiring a signal relative to the lighting of the photodiode; and determining, from the acquired signal, a measurement representative of a contamination status by metallic atoms of the photodiode.

21 Claims, 4 Drawing Sheets

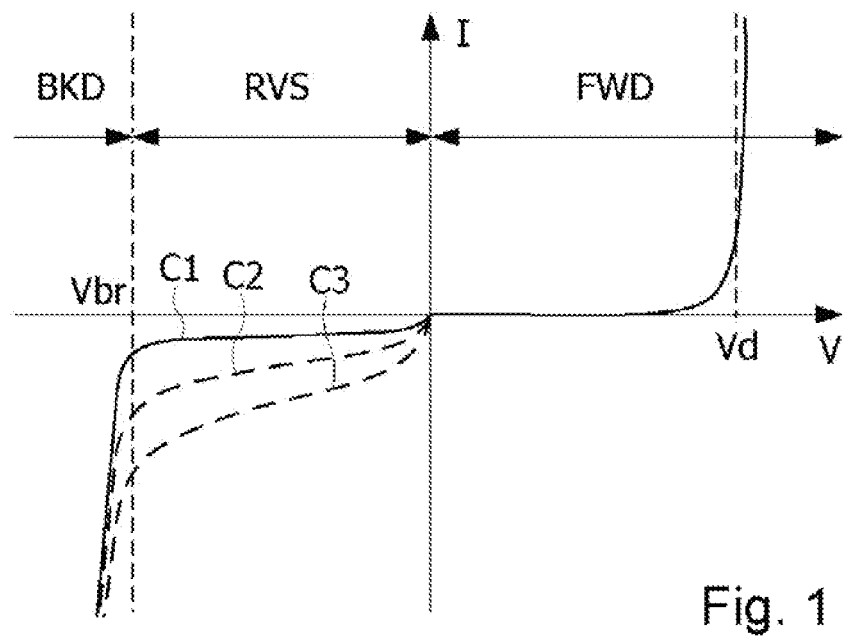
Fig. 1
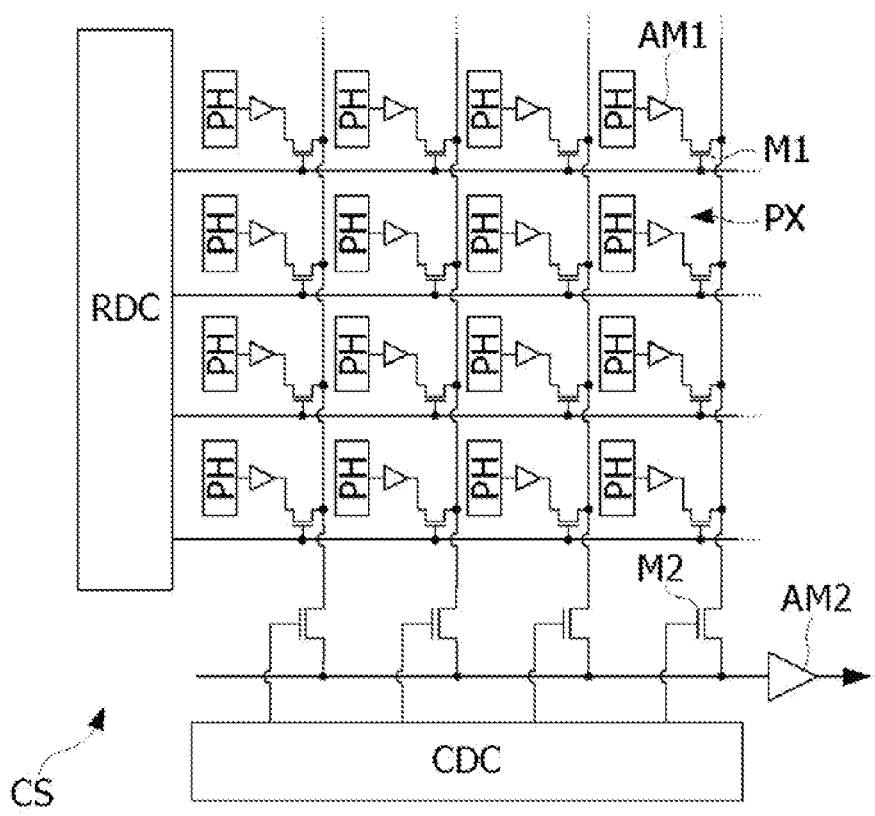
Fig. 2 *(Prior Art)*

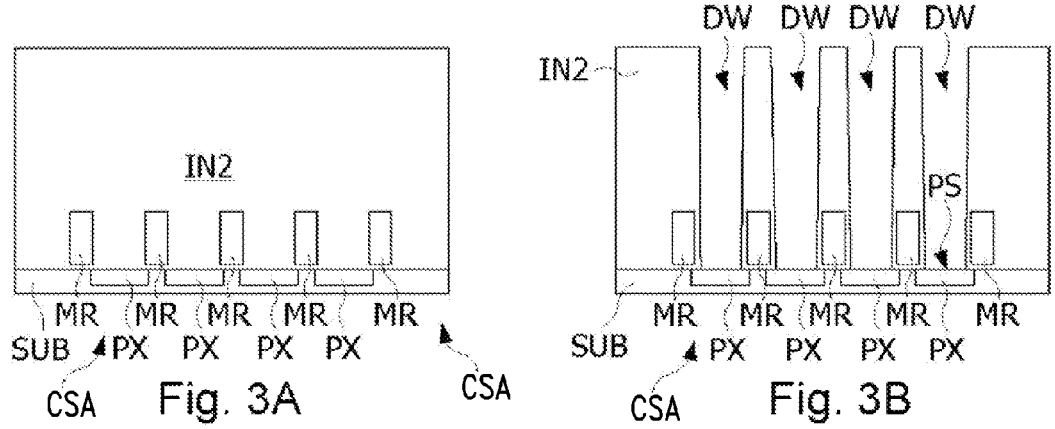
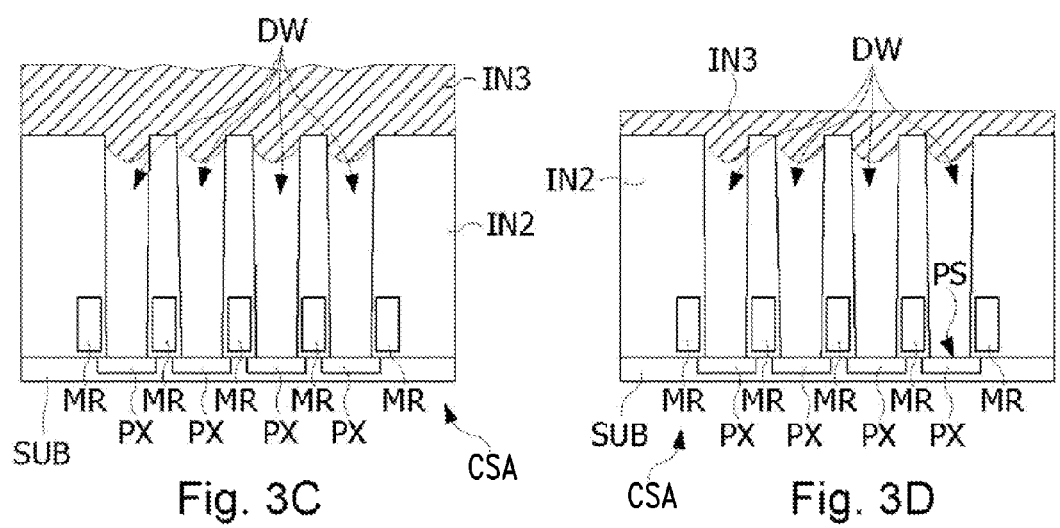

METHOD AND DEVICE FOR DETECTING METALS IN A FLUID

BACKGROUND

1. Technical Field

The present disclosure relates to the detection of metals in a fluid such as water or air. The present disclosure relates in particular to the detection of pollution by heavy metals.

2. Description of the Related Art

Certain metals produced by human activity are rejected into nature and cause pollution of the water or of the air. Certain metals such as arsenic, cadmium, chromium, copper, mercury, nickel, lead, and zinc effect health and the biosphere. It is therefore desirable to detect the presence of such metals.

In the semiconductor component manufacturing industry, certain manufacturing steps use ultrapure water. It is therefore also desirable in this domain to be able to detect the presence of metals in the water used in order to prevent any metallic contamination of manufactured components.

Among the known detection and analysis methods are spectrometry methods by absorption or by plasma emission, methods based on the fluorescence under the effect of X-rays, and colorimetric methods. These methods require expensive equipment as well as the sampling and transport of water samples to a laboratory where the samples may be analyzed. Certain analysis methods require pre-treatments such as filtration and the addition of chemical additives. These methods have the disadvantages of being long, expensive, and unreliable due to the non-negligible risk of sample contamination during their transport, storing, or pre-treatment.

Electrochemical detection and analysis methods also exist that are in-situ, that is to say that they do not require transport and storing of samples, nor pre-treatment. These methods measure one or more electrical characteristics of a sample, such as the intensity of a current traversing the sample, the voltage between electrodes inserted in the sample, and the electrical resistance of the sample. The detection or the analysis is done from the measured electrical characteristics.

Recently, electrochemical microsensors formed in a film have also been developed.

BRIEF SUMMARY

One embodiment of the present disclosure is a method for detecting traces of metals that is inexpensive, all while allowing a high detection sensibility. To this end, it is based on the discovery that a photodiode that has been contaminated by metal atoms, for example during its fabrication, supplies in the absence of light a signal larger than that of an uncontaminated photodiode.

Embodiments of the disclosure relate to a method for detecting metallic atoms in a fluid comprising the steps of: placing, in a zone sheltered from light, a photodiode comprising a photosensitive surface in contact with a fluid to analyze; heating the photosensitive surface of the photodiode to a temperature sufficient to allow metallic atoms deposited on the photosensitive surface to migrate through the photosensitive surface; acquiring a signal relative to the lighting of the photodiode; and determining, from the acquired signal, a measurement representative of a contamination status by metallic atoms of the photodiode.

According to one embodiment, the method comprises a step of regulating the temperature of the fluid near the photodiode, to maintain it at an essentially constant value.

According to one embodiment, the method comprises steps of measuring the temperature of the fluid near the photodiode and of correcting the measurement representative of a contamination status of the photodiode as a function of the measured temperature.

According to one embodiment, the steps of heating the photosensitive surface of the photodiode, of acquiring a signal representative of the lighting of the photodiode, and of determining a measurement, are performed periodically.

According to one embodiment, the measurement is corrected by subtracting from an initial measurement or a preceding measurement.

According to one embodiment, the photodiode belongs to an imager comprising a plurality of photodiodes and a photosensitive surface through which the metallic atoms deposited on the imager can migrate, the method comprising steps of acquiring signals relative to the lighting of photodiodes of the imager and of determining a measurement representative of a contamination status of the imager as a function of acquired signals.

According to one embodiment, the method comprises steps of covering the photosensitive surface of the imager with a layer of an isolating material, and of forming wells in the isolating layer to allow metallic atoms to reach the PN junction of photodiodes of the imager.

According to one embodiment, the method comprises steps of depositing a protective layer on the isolating layer, and of removing the protective layer at the commissioning of the imager.

Embodiments of the disclosure also relate to a device for detecting metallic atoms in a fluid, wherein the device is configured to implement the method according to one of the embodiments described above.

According to one embodiment, each photodiode comprises a PN junction not covered by a doped region.

According to one embodiment, the device comprises an isolating layer covering the photosensitive surface of each photodiode, the isolating layer comprising a well allowing metallic atoms to reach the photosensitive surface of each photodiode.

According to one embodiment, the device comprises a resistive ring formed around the well to heat the photosensitive surface of the photodiode to a temperature sufficient to allow metallic atoms deposited on the photosensitive surface of the photodiode to migrate in the semiconductor material in which the photodiode is formed.

According to one embodiment, the device comprises a temperature sensor to measure the ambient temperature near the photodiode.

According to one embodiment, the device comprises an imager comprising a plurality of photodiodes, and a photosensitive surface covered by an isolating layer pierced with wells allowing metallic atoms to reach the photosensitive surface of each photodiode.

According to one embodiment, each well is covered by a protective layer destined to be removed at the commissioning of the device.

BRIEF DESCRIPTION OF THE SEVERAL VIEWS OF THE DRAWINGS

Embodiment examples of the disclosure will be described in the following, in a non-limiting manner, in relation with the appended drawings, among which:

FIG. 1 shows variation curves of current traversing a photodiode as a function of the biasing voltage of the photodiode, FIG. 2 schematically shows an electronic circuit of a conventional CMOS type imager, FIGS. 3A to 3D show manufacturing steps of a metal detector, according to an embodiment.

DETAILED DESCRIPTION

Figure 4:
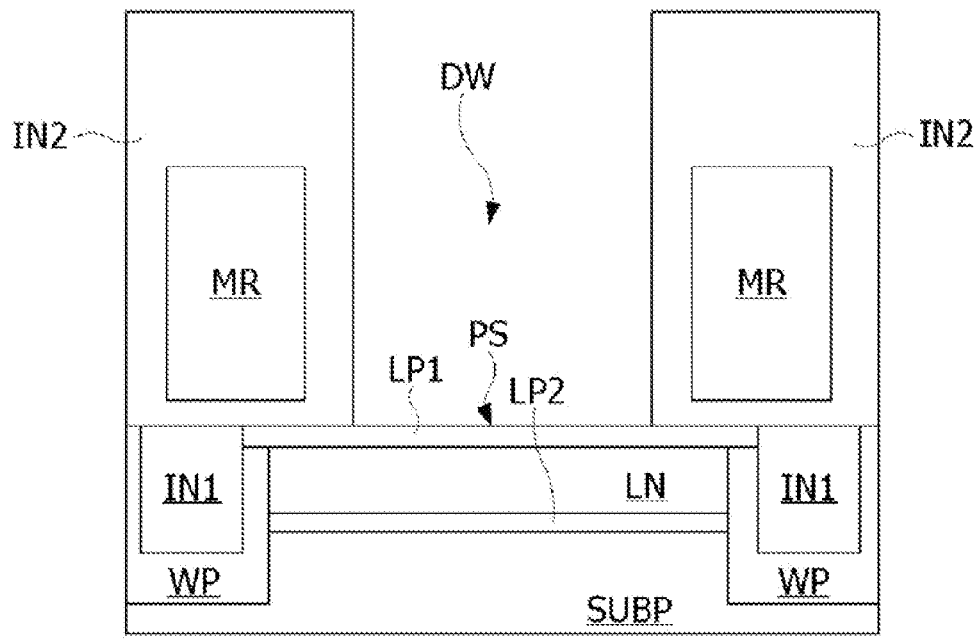
FIGS. 4 and 5 show, in transversal cross-section, a photodiode formed in a semiconductor substrate, according to two embodiments.

FIG. 1 shows variation curves of the current traversing a photodiode as a function of a biasing voltage of the photodiode. FIG. 1 shows three operating zones of a photodiode, delimited as a function of the voltage supplied between the terminals of the photodiode. The photodiode has an operating zone FWD when it is directly biased. In this operating zone, the current traversing the photodiode remains substantially zero until a value Vd, where the photodiode becomes conducting and lets all the current pass.

When it is inversely biased, the photodiode has two operating zones RVS and BKD. In the zone RVS, the photodiode lets a non-zero current pass in the absence of light (curve C1), which progressively increases (curves C2, C3) as a function of the luminous intensity to which the photodiode is subjected. When the inverse bias voltage reaches a value Vbr, operating zone BKD is reached. In this zone, an avalanche phenomenon is launched in the photodiode, allowing a large inverse current to pass.

To measure a luminous intensity, the photodiode is therefore inversely biased, thus in the functioning zone RVS. In this zone, the current Ir traversing the diode may be modeled by the following equation:

$$Ir = Id + Ip \quad (1)$$

wherein Id represents a parasitic current generated by the photodiode in darkness (in the absence of a luminous flux) and Ip represents the current generated by the photodiode under the effect of a luminous flux. The current Ip is generated by certain photons of the luminous flux having enough energy to generate free electrons, forming the generated current. The current Ip is proportional to the intensity of the luminous flux received by the photodiode. The current Id is equal to a current It that depends on the ambient temperature. The current It may be modeled by the following equation:

$$It = Is(1 - e^{\frac{-qVr}{kT}}) \quad (2)$$

wherein Is is a constant, q is the electric charge of a carrier (electron/hole), K is the Boltzmann constant, Vr is the inverse bias voltage of the photodiode, and T is the ambient temperature. In other words, the current It results from the generation by thermal effect of free electrons and holes near the PN junction forming the photodiode. In CMOS technology at 0.18 μm, the current It is on the order of 2.10 exp−18 A at 25° C.

It has been discovered that in the presence of metallic atoms near or in the PN junction of the photodiode, the current Id is larger because of the appearance of a current Ic due to the presence of such atoms. The current Id generated by the inversely biased photodiode, in the absence of light, may therefore be modeled by the following equation:

$$Id = It + Ic \quad (3)$$

Indeed, the presence of metallic atoms near the PN junctions increases the number of electron-hole pairs at a given temperature. One embodiment of the present disclosure exploits this phenomenon to detect the presence of metals in a fluid such as water or air. A CMOS imager having a low cost and a large number of photodiodes appears well-adapted to this end.

FIG. 2 shows a conventional CMOS imager CS comprising a matrix of pixels PX arranged in rows and in columns transversal to the rows. Each pixel PX comprises a photodiode PH, an amplifier AM1 to amplify the current supplied by the photodiode, and a selection transistor M1 to allow the pixel to be read, that is to say the acquisition of a signal representative of a luminous flux received by the photodiode. The gates of transistors M1 of each row of pixels are connected to a row decoder circuit RDC thus allowing the signals supplied by each row of pixels to be acquired. Each column of pixels has the drains of transistors M1 connected to a column selection transistor M2, the gate of which is controlled by a column decoder circuit CDC. The drains of transistors M2 are connected to an amplifier AM2. The amplifier supplies the signal of a pixel selected by the row decoder RDC by the intermediary of the pixel's transistor M1 and by the column decoder CDC by the intermediary of the transistor M2 of the column of pixels to which the selected pixel belongs.

FIGS. 3A to 3D show manufacturing steps of an imager CSA usable as a metal detector according to one embodiment of the present disclosure, after pixels PX have been formed in a semiconductor substrate SUB. The imager CSA can include the conventional imager CS shown in FIG. 2, together with additional elements configured to enable the imager CSA to be used in a metal detector. FIG. 3A shows steps of depositing an isolation layer IN2 on the substrate SUB and of forming resistive rings MR around pixels PX, the resistive rings being embedded in the layer IN2.

Each resistive ring MR has a function of heating a corresponding photodiode PH in order to facilitate the migration of metallic atoms present at the photosensitive surface PS of the photodiode in the PN junction zone of the photodiode. To this end, each resistive ring MR is configured to be linked to an electric current source in order to give off the heat to heat a photodiode, for example to a temperature on the order of 300 to 400° C. Each resistive ring MR is for example made of tungsten.

FIG. 3B shows a step of forming wells DW in the layer IN2 to clear the photosensitive surface PS of the photodiode of each pixel PX. These wells may be made for example by photolithography. The width of wells DW is adapted to the width of pixels PX and may reach for example 0.25 μm for a depth of 1.3 μm. The depth of wells DW corresponds substantially to the thickness of the isolation layer IN2, so as to leave only a very thin isolation layer on the semiconductor forming the photodiodes. Evidently, the thickness of the isolation layer that may remain above the photodiodes influences the quantity of metallic atoms susceptible of reaching the PN junctions of the photodiodes and therefore the sensibility of detecting such atoms.

FIG. 3C shows a step of depositing another protective layer IN3 on the layer IN2 and extending partially in its wells DW. This step aims to temporarily close the wells DW, and thus to avoid dust and metallic atoms reaching the surface of the substrate (photosensitive surface PS) before the commissioning of the detector.

FIG. 3D shows a step of reducing the thickness of the protective layer IN3. This step may be done by mechanical polishing. This step is optional and depends on the thickness of the layer IN3 after the deposition of layer IN3 (FIG. 3C). The protective layer IN3 is configured to be removed at the commissioning of the detector, to open the wells DW and thus to allow metallic atoms to penetrate the wells and to reach the photodiodes of the imager CS. The removal of the layer IN3 may be done by abrasion, for example with the aid of an abrasive diamond paper.

Evidently, the steps shown by FIGS. 3C and 3D may be replaced by other methods, for example by the use of an adhesive film disposed on the layer IN2 in order to cover the wells DW, and configured to be removed at the commissioning of the detector.

It should be noted that the imager CSA differs from the conventional imager CS in that the photosensitive surface PS is left open to air or is covered by a thin isolation film. On the contrary, in conventional imagers, the zones of the substrate forming the pixels are covered by colored filters and by microlenses.

FIG. 4 shows one of the photodiodes PH formed in the semiconductor substrate SUB of the imager CSA. The substrate is lightly doped by a P type doping. The photodiode PH comprises a thin P doped layer LP2, formed in the depth of the substrate, an N doped layer LN formed above the layer LP2, and a superficial thin P+ doped layer LP1, formed above the layer LN. The interfaces between the layer LN and the layers LP1 and LP2 form the PN junctions of the photodiode. The top surface (in the figure) of the layer LP1 constitutes the photosensitive surface PS of the photodiode PH. Each photodiode PH is laterally isolated from other photodiodes PH formed in the substrate SUB by isolation zones IN1 that may be formed in P+ doped wells WP. The layer LP1 is covered by the isolating layer IN2 in which a resistive ring MR is formed and a well DW at the center of the ring MR, reaching the layer LP1 (photosensitive surface PS) or leaving a thin isolating film on the layer LP1.

Figure 5:
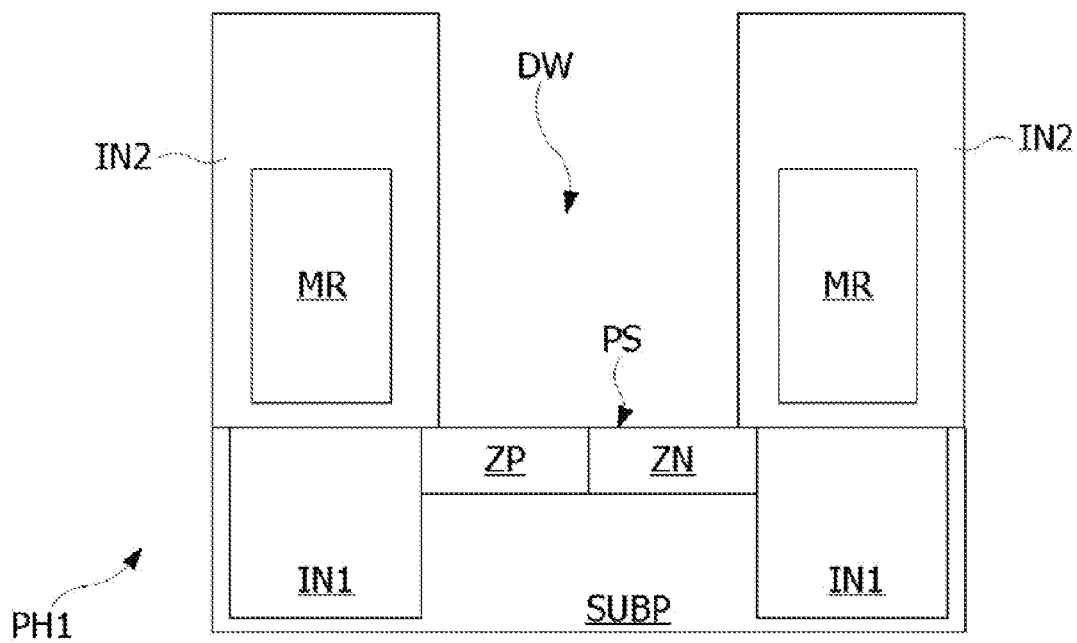

FIG. 5 shows a photodiode PH1 formed in a semiconductor substrate SUB, according to another embodiment. The substrate is lightly doped by a P type doping. The photodiode PH1 comprises two adjacent zones formed at the surface of the substrate, that is a P doped zone ZP and an N doped zone ZN. The photodiode PH1 is laterally isolated from other adjacent photodiodes made in the substrate SUB by an isolating zone IN1 formed in the substrate around zones ZP and ZN. As previously described in reference to FIGS. 3A to 3D, the substrate SUB is covered with an isolating layer IN2 that is pierced with a well DW above each photodiode, to clear the zones ZP and ZN. The isolating layer IN2 surrounds the resistive rings MR formed around each photodiode PH1. Thus, the PN junction formed by the zones ZP, ZN, is directly exposed at the surface of the substrate SUB, constituting the photosensitive surface PS of the photodiode PH1. This arrangement allows for a reduction of the time for a contamination atom to reach the sensitive zone where it will be detectable.

In the embodiments of FIGS. 4 and 5, the structure of the photodiodes (dimensions and forms of the doped zones, doping intensities) may be adapted to obtain a desired detection sensitivity.

Figure 6:
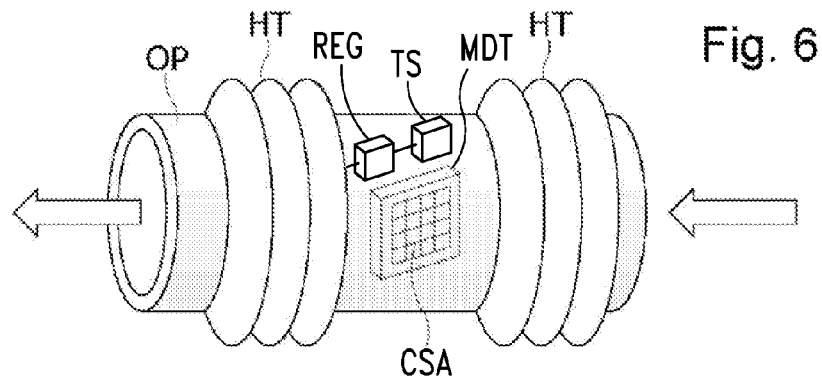
FIG. 6 shows a metal detector, according to an embodiment, installed in a pipe through which fluid to analyze circulates, FIG. 7 schematically shows an electronic circuit of the detector according to an embodiment.

FIG. 6 shows a metal detection device MDT, according to an embodiment. The device MDT is installed in a pipe OP through which the fluid to analyze circulates. The device MDT comprises an imager such as the imager CSA previously described. The pipe OP is configured to maintain the imager CSA sheltered from light. To this end, the pipe OP may have for example twists and turns (not shown). The temperature of the fluid in the pipe may be regulated in order to be maintained at a constant set point value. To this end, the pipe may be equipped with heaters HT, a temperature sensor TS, and a regulation circuit REG connected to the temperature sensor and to the heaters HT. The heaters may comprise a resistive wire wrapped around the pipe OP. In another embodiment, the heaters may be coupled directly to the detection device MDT. In another embodiment, the heaters may be omitted. The measurements supplied by the imager may therefore be corrected by taking into account the temperature of the imager, supplied by a temperature sensor.

Figure 7:
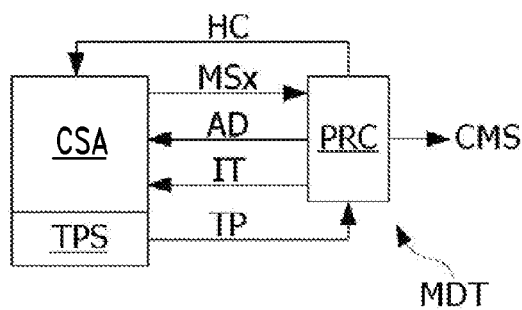

FIG. 7 shows electronic circuits of the metal detection device MDT. In FIG. 7, the device MDT comprises the imager CSA and a processor PRC connected to the imager CSA. The processor, for example of the microprocessor or microcontroller type, controls the integration time IT of pixels PX of the imager CSA, and controls the heating of the photodiodes of the imager by controlling the provision of a supply current HC to the resistive rings MR around the photodiodes of the imager. The processor PRC supplies selection addresses AD of pixels PX of the imager and receives in return read signals MSx of the selected pixels. The imager CSA may be coupled to a temperature sensor TPS supplying temperature measurements TP of the imager to the processor PRC. The ensemble of circuits shown in FIG. 7 may be integrated in a single component.

Figure 8:
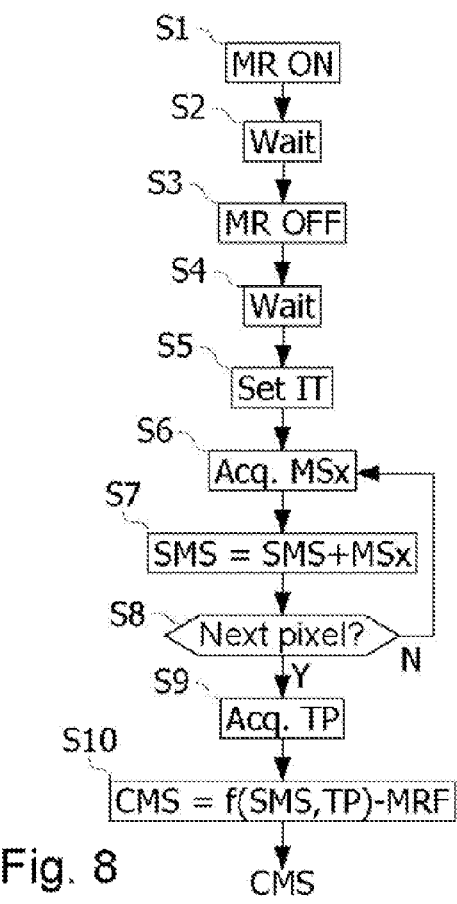
FIG. 8 shows a sequence of steps performed by the electronic circuit of FIG. 7.

The imager CSA may be controlled by the processor PRC to periodically perform a contaminant measurement phase. FIG. 8 shows a sequence of operations that may be executed by the processor PRC during such a measurement phase. Each measurement phase comprises steps S1 to S3 of activation of the electrical supply to the resistive rings MR around photodiodes of the imager CSA. The duration of the activation of the resistive rings MR is adapted to allow contaminant elements that might have been deposited on the sensitive surface of the photodiodes PH, PH1 to diffuse into the semiconductor substrate near the PN junctions forming the photodiode. The heating step is followed by a rest step S4 during which the rings MR are no longer powered and cool down. The rest step S4 is followed by a control step S5 of the integration time IT of pixels PX of the imager CSA. This step is followed by a read sequence, comprising steps S6 to S8, of the imager CS. This sequence consists of selecting, successively or by groups, all or only some of the pixels PX of the imager, acquiring a signal from each pixel or group of pixels, and deducing a measurement from each pixel or group of pixels (step S6). At step S7, the measurements obtained are added with one another. The sum of the measurements is considered to be a contamination measurement SMS.

Once all the pixels have been read, the processor may perform a temperature acquisition at step S9, and determine at step S10 a corrected contamination measurement f(SMS, TP) as a function of the acquired temperature TP and of the measurement SMS obtained following steps S6 to S8. The function f allowing the corrected contamination measurement to be determined, may be determined during a calibration phase. Curves or graphs may be established giving a correction value to add to or to subtract from the measurement SMS, as a function of the ambient temperature TP and possibly as a function of the measurement itself, to obtain a measurement at a reference temperature, for example at 20° C. It should be noted that the steps S9 and S10 may be omitted if the pipe OP or the device MDT is equipped with the regulator REG configured to regulate the ambient temperature. It should also be noted that the measurement of temperature TP may also be done before the signals from the imager CSA are acquired (before step S6).

The sequence of steps of FIG. 8 may be executed a first time during an initialization phase of the detector MDT, without activating the resistive rings MR, to obtain a reference measurement MRF representative of the state of the imager CS at its commissioning. A corrected contamination measurement may then be obtained by subtracting a temperature corrected measurement f(SMS, TP) from the reference measurement MRF to obtain a value CMS representative of a contamination status of the imager CS.

As the detection device functions by accumulating metallic contaminants, the concentration of contaminant atoms increases with time. A value representative of the evolution of the contamination status may therefore also be calculated by subtracting, from each corrected measurement, the corrected measurement obtained during the preceding measurement phase.

Thanks to these dispositions, the detection device has a very low cost. This device allows the contamination status of a fluid to be monitored in real time, without needing to take samples, without any chemical reaction, and without requiring a preceding treatment of samples. This device also has a high sensitivity, while being capable of detecting traces of metals in a fluid such as air or water.

It will clearly appear to the skilled person that disclosure is susceptible of diverse variations of implementation and applications. In particular, the disclosure is not limited to a detector comprising an imager, but may be made from a single photodiode such as the photodiode PH or PH1 previously described. The implementation of several photodiodes by the intermediary of an imager simply allows the sensitivity of the detector to be increased.

It is also not necessary to place the detector in a pipe through which the fluid to analyze circulates. It suffices that the detector, and in particular the photosensitive surface of the photodiode or of the imager, be in contact with the fluid to analyze.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:
    detecting metallic atoms in a fluid, the detecting including:
        placing, in a zone sheltered from light, a photodiode having a photosensitive surface in contact with at least some of the metallic atoms of the fluid,
        heating the photosensitive surface of the photodiode to a temperature sufficient to allow metallic atoms deposited on the photosensitive surface to migrate through the photosensitive surface,
        acquiring a sensing signal representative of the metallic atoms migrating through the photosensitive surface, and
        determining, from the acquired signal, a measurement representative of a contamination status by metallic atoms of the photodiode.

2. A method according to claim 1, comprising regulating a temperature of the fluid near the photodiode, the regulating including maintaining the temperature of the fluid at a substantially constant value.

3. A method according to claim 1, comprising measuring the temperature of the fluid near the photodiode and correcting the measurement representative of the contamination status of the photodiode as a function of the measured temperature.

4. A method according to claim 1, wherein the heating, acquiring, and determining are performed periodically.

5. A method according to claim 4, wherein the measurement is corrected by subtracting an initial measurement or a preceding measurement.

6. A method according to claim 1, wherein the photodiode is part of an imager that includes a plurality of photodiodes and with respective photosensitive surfaces through which the metallic atoms can migrate, the method comprising acquiring signals relative to lighting of the plurality of photodiodes of the imager and determining a measurement representative of a contamination status of the imager as a function of acquired signals.

7. A method according to claim 6, wherein the imager includes a layer of an isolating material, and wells in the isolating layer that allow metallic atoms to reach the photosensitive surfaces of the photodiodes of the imager.

8. A method according to claim 7, wherein the imager includes a protective layer on the isolating layer, and the method includes removing the protective layer prior to the detecting.

9. A device for detecting metallic atoms in a fluid, comprising:
    a zone sheltered from light,
    a photodiode positioned in the zone and having a photosensitive surface configured to contact at least some of the metallic atoms of the fluid, the photodiode being configured to produce a sensing signal representative of the metallic atoms migrating through the photosensitive surface,
    a heater configured to heat the photosensitive surface of the photodiode to a temperature sufficient to allow metallic atoms deposited on the photosensitive surface to migrate through the photosensitive surface, and
    a processor configured to determine, from the sensing signal, a measurement representative of a contamination status by the metallic atoms in the fluid.

10. A device according to claim 9, wherein the photodiode comprises a PN junction not covered by a doped region.

11. A device according to claim 9, comprising:
    a semiconductor substrate in which the photodiode is integrated; and
    an isolating layer on the substrate, the isolating layer including a well configured to allow metallic atoms to reach the photosensitive surface of the photodiode.

12. A device according to claim 11, wherein the heater includes a resistive ring formed around the well and configured to heat the photosensitive surface of the photodiode to a temperature sufficient to allow metallic atoms deposited on the photosensitive surface of the photodiode to migrate in semiconductor material of the photodiode.

13. A device according to claim 9, comprising a temperature sensor configured to measure an ambient temperature near the photodiode.

14. A device according to claim 9, wherein the photodiode is one of a plurality of photodiodes, with respective photosensitive surfaces, the device including:

an isolating layer formed on the photodiodes and pierced with wells configured to allow metallic atoms to reach the photosensitive surface of each photodiode.

15. A device according to claim 14, comprising a protective layer covering the wells and configured to be removed at a commissioning of the device.

16. A device according to claim 9, wherein the zone is an interior of a pipe configured to receive the fluid.

17. A metal detector, comprising:
a photodiode having a photosensitive surface configured to contact at least some metallic atoms of a fluid, the photodiode being configured to produce a sensing signal representative of metallic atoms migrating through the photosensitive surface; and
a heater configured to heat the photosensitive surface of the photodiode to a temperature sufficient to allow metallic atoms contacting the photosensitive surface to migrate through the photosensitive surface.

18. A metal detector according to claim 17, comprising:
a semiconductor substrate in which the photodiode is integrated; and
an isolating layer on the substrate, the isolating layer including a well configured to allow metallic atoms to reach the photosensitive surface of the photodiode.

19. A metal detector according to claim 18, wherein the heater includes a resistive ring formed around the well and in the isolating layer.

20. A metal detector according to claim 18, a protective layer covering the well and configured to be removed at a commissioning of the metal detector.

21. A metal detector according to claim 17, comprising:
a processor configured to determine, from the sensing signal, a measurement representative of a contamination status by the metallic atoms in the fluid.

* * * * *